US005914105A

United States Patent [19]

Barcay et al.

[11] Patent Number: 5,914,105
[45] Date of Patent: Jun. 22, 1999

[54] PETROLEUM BASED PEST BAIT

[75] Inventors: Stephen John Barcay, Burnsville; Douglas G. Anderson, Lakeville, both of Minn.

[73] Assignee: Ecolab Inc., St. Paul, Minn.

[21] Appl. No.: 08/554,094

[22] Filed: Nov. 6, 1995

Related U.S. Application Data

[63] Continuation-in-part of application No. 08/261,461, Jun. 17, 1994, Pat. No. 5,464,613.

[51] Int. Cl.$^6$ .......................... A01N 25/00; A01N 57/12; A01N 57/16; A01N 59/14

[52] U.S. Cl. ........................ 424/84; 514/118; 514/120; 514/772; 514/788.1; 514/789; 43/121; 426/1

[58] Field of Search .................. 424/84; 514/89, 514/118, 120, 772, 788.1, 789; 43/121, 132.1; 426/1

[56] References Cited

U.S. PATENT DOCUMENTS

| | | | |
|---|---|---|---|
| 3,716,600 | 2/1973 | Magee | 558/178 |
| 3,845,172 | 10/1974 | Magee | 558/178 |
| 3,887,710 | 6/1975 | Shaver et al. | 424/300 |
| 4,049,460 | 9/1977 | Broadbent | 424/84 |
| 4,388,297 | 6/1983 | Naffziger | 514/89 |
| 4,696,822 | 9/1987 | Matsumura et al. | 424/490 |
| 4,823,506 | 4/1989 | Demarest et al. | 43/131 |
| 4,841,669 | 6/1989 | Demarest et al. | 43/131 |
| 4,863,718 | 9/1989 | Bernardo | 424/40 |
| 4,889,710 | 12/1989 | Hagarty | 424/45 |
| 4,959,221 | 9/1990 | Holmes | 424/659 |
| 4,988,511 | 1/1991 | Demetre | 424/84 |
| 4,988,516 | 1/1991 | Herring | 424/659 |
| 5,104,658 | 4/1992 | Hagarty | 424/405 |
| 5,116,618 | 5/1992 | Hagarty | 424/405 |
| 5,326,560 | 7/1994 | Henderson et al. | 514/65 |
| 5,346,700 | 9/1994 | Stapleton et al. | 424/410 |
| 5,401,506 | 3/1995 | Chang et al. | 424/408 |
| 5,547,955 | 8/1996 | Silerman et al. | 514/275 |

FOREIGN PATENT DOCUMENTS

| | | |
|---|---|---|
| 576034 | 6/1986 | Australia . |
| 0 028 18 | 5/1981 | European Pat. Off. . |
| 0 638 237 A1 | 8/1991 | European Pat. Off. . |
| 218110 | 11/1989 | New Zealand . |
| 231539 | 3/1991 | New Zealand . |
| 416927 | 9/1934 | United Kingdom . |
| WO 91/07972 | 6/1991 | WIPO . |

OTHER PUBLICATIONS

Arthur G. Appel, *Laboratory and Field Performance of Consumer Bait Products for German Cockroach(Dictyopters: Blattellidae) Control*, Entomological Society of America 1990, pp. 153–159.

E. Paul Wileyto et al., *Attraction of the German Cockroach, Blattella germanica (Orthoptera: Blatellidae), to Some Volatile Food Components*, Journal of Economic Entomology, vol. 76, No. 4, 1983, pp. 752–756.

Arthur G. Appel, *Performance of Gel and Paste Bait Products for German Cockroach (Dictyoptera: Blattellida ) Control: Laboratory and Field Studies*, Entomological Society of America, vol. 85, No. 4, Aug. 1992, pp. 1176–1183.

Michael K. Rust, "Managing Household Pests", *Advances in Urban Pest Management*, G.W. Bennet and M. Owens (eds), Van Norstrand Reinhold, New York 1986, pp. 335–368.

William H. Robinson, *Proceedings of the National Conference on Urban Entomology*, 1992, pp. 77–91.

Michael K. Rust et al., *Attraction and Performance of Insecticidal Baits for German Cockroach Control*, International Pest Control 1981, pp. 106–109.

Hideakir Tsuji, *Attractive and Feeding Stimulative Effect of Some Fatty Acids and Related Compounds on Three Species of Cockroaches*, Japanese Journal of Sanitary Zoology 1966, pp. 89–96.

Kepner, R.L. et al., "Development of a Toxic Bait for Control of Mole Crickets (Orthoptera: Gryllotalpidore)," Journal of Economic Entomology, Vol. 80(3), 1987, pp. 659–665.

Search Report from UK Patent Office, Jan. 8, 1997.

Ballard, J.B. et al., "Laboratory and field evaluations of German cockroach (Orthoptera:Blattelidae) traps," Journal of Economic Entomology, vol. 77, No. 3, pp. 661–665, 1984.

*Primary Examiner*—John Pak
*Attorney, Agent, or Firm*—Merchant, Gould, Smith, Edell, Welter & Schmidt, P.A.

[57] ABSTRACT

Novel fat-like petroleum based, water-free, insecticidal compositions are described which are particularly effective against insect pests such as cockroaches, ants, termites, flies, etc. The compositions may be used in various forms depending on the targeted pests. As an example, the composition in the form of a paste can be applied into cracks and crevices for control of such pests and have the advantage of superior durability and prolonged attractiveness.

2 Claims, 12 Drawing Sheets

PETROLEUM BASED PEST BAIT

CROSS REFERENCE TO RELATED APPLICATION

This application is a continuation-in-part of U.S. patent application Ser. No. 08/261,461, filed Jun. 17, 1994 which is now U.S. Pat. No. 5,464,613.

FIELD OF THE INVENTION

This invention relates to water free, thick liquid, or semi-solid petroleum based pest baits for controlling insect pests such as flying and crawling insects, including, for example, cockroaches, ants, termites, flies, etc.

BACKGROUND OF THE INVENTION

Historically, toxic baits for controlling crawling insects, such as cockroaches, have been water-based. With cockroaches especially, water is presumed necessary for good bait performance. Unfortunately, water-based bait products rapidly lose effectiveness due to water loss, spoilage, rancidity or breakdown of active ingredients and other factors. Studies of water-based paste baits have confirmed that water loss, repellant properties of active ingredients, and insecticide resistance are the most important factors affecting bait performance, Appel, A. G. *J. Econ Entomol* 85 (4):1176–1183 (1992), Robinson, W. H. *Proceedings of the National Conference on Urban Entomology* 77–91 (1992), and Rust, N. K. "Managing Household Pests", in *Advances in Urban Pest Management*, G. W. Bennett and M. Owens (eds), Van Norstrand Reinhold, New York 335–368 (1986).

The above problems have been solved by developing superior baits that are fat-based suspensions, designed to be applied, for example, as pastes to cracks and crevices for control of cockroaches, ants and other insects. These fat-based baits have the advantage of superior durability with prolonged attractiveness and stability of active and inert ingredients. Fat-based baits have the additional advantage of water repellency, allowing for durability in excessively damp environments. In some environments stability and browning remain a problem in certain formulations.

SUMMARY OF THE INVENTION

The present invention provides for a more stable and thus more insect-palatable and longer effective insect pest bait composition than prior compositions previously known. Accordingly, the present invention is a water-free, or substantially water-free, insecticidal composition for use against insect pests containing an effective amount of insecticide in admixture with a fatty (triglyceride-like) petroleum based carrier.

A second aspect of the present invention is a water-free insecticidal composition for use against insect pests including:
  (i) about 0.01–5.0 wt % of an insecticide selected from the group consisting of an organophosphate, a carbamate, a pyrethroid, an amidinohydrazone, an avermectin, and a chlorinated hydrocarbon, and
  (ii) about 20–60 wt % of a fat-like petroleum based carrier.

A third aspect of the present invention is a water-free insecticidal composition for use against insect pests containing:
  (i) about 5–60 wt % boric acid; and
  (ii) about 20–60 wt % of a fat like petroleum based carrier.

Finally, the fourth aspect of the present invention is a method of controlling insect pests by applying to areas to be controlled the above water-free insecticide compositions.

BRIEF DESCRIPTION OF THE DRAWINGS

FIG. 1 shows results of a stability (browning) study, FIG. 2 is a palatability study results and FIGS. 3 through 6 are mortality results.

FIG. 7 and 8 are results of comparative stability (browning) and palatability studies among compositions of the present invention and a wax based composition. FIG. 9 through 11 are results of efficacy studies (mortality) of boric acid compositions of the present invention.

FIGS. 12 through 16 show graphic results of studies carried out similarly to those shown in FIGS. 7 through 11 where chlorpyrifos is the insecticide.

DETAILED DESCRIPTION OF THE INVENTION

Figure 1:
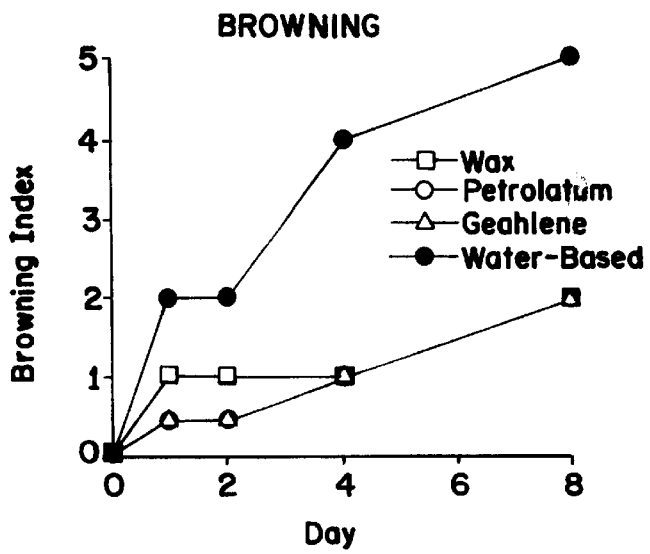
FIGS. 1–6 show graphic results of comparative studies among compositions of the present invention and a water-based composition where the insecticide is acephate.
Figure 2:
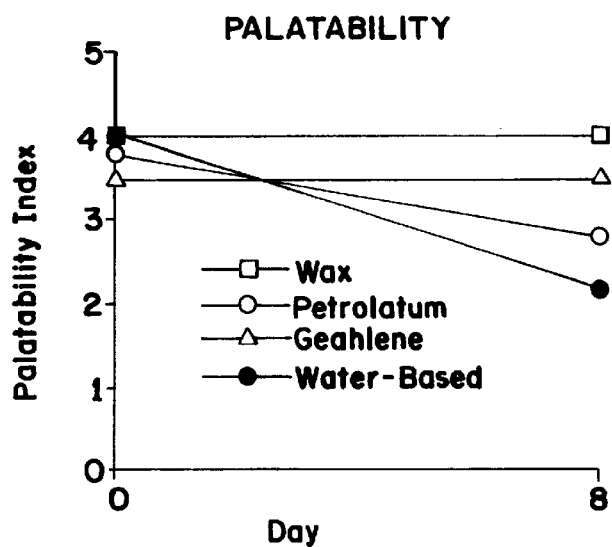

The petroleum based baits of the present invention are preferably used in the form of a paste and are substantially free of water, i.e. free of added water. These thickened bait compositions may be modified by manufacturing to form a variety of different formulations and textures in addition to pastes, for example, granules, dusts, pellets, and the like. The use of the composition in containerized or non-containerized forms is designed against a wide variety of pests such as and including a wide variety of insects such as but not limited to, cockroaches, ants, crickets, termites, flies and the like.

Since the present invention is directed to the concept of a formulation which is essentially petroleum based and substantially water-free, it can include, in this composition, any insecticide. Included as examples of active ingredients are compounds from the following classes of insecticides:

1—organophosphates, e.g. acephate, chlorpyrifos or diazinon;
  2—mineral acids, e.g. boric acid;
  3—carbamates, e.g. propoxur, 2-(1,3-dioxolane-2-yl)-phenyl-N-methyl carbamate, or o-isopropoxy-phenylmethylcarbamate;
  4—pyrethroids, e.g. cyfluthrin, or deltamethrin;
  5—amidinohydrazones, e.g. hydramethylnon;
  6—avermectins, e.g. abamectin;
  7—chlorinated hydrocarbons, e.g. lindane, and combinations of the above with known synergists, such as carbamates or pyrethroids, e.g. o-isopropoxy-phenylmethylcarbamate or 2-(1,3-dioxolane-2-yl)-phenyl-N-methylcarbamate in combination with piperonyl butoxide or piperonal bis-(2,2-butoxyethoxy)-ethyl acetal.

The term "fat-like petroleum based material" is meant to include non-toxic hydrocarbon based cuts from the petroleum industry. The term is meant to include thick semi-solid or solid materials that can be blended with the active pesticide ingredients of the invention and with other inert components. The term includes substantially hydrocarbon materials having similar blending, water repellency properties and viscosity as typical fatty triglycerides. The term includes materials that are clear and water white or translucent. Broadly the terms includes white oils, purified mineral oils, polyisobutylene polymers, etc. These materials are either directly derived from petroleum feed stocks or are prepared by the polymerization of olefinic refinery streams into inert nontoxic polymeric materials of appropriate viscosity. The term further includes formulated materials that can be prepared by thickening or gelling the petroleum based material. Common gelling agents including both organic and inorganic gelling agents can be used. Such gelling agents include inorganic salt such as calcium carbonate, magnesium carbonate, silicon dioxide, etc. A variety of organic thickening agents are also known but are not preferred. The term is also meant to include a silicone oil which is a hydrocarbon substituted siloxane. Such oils are typically made by obtaining hydrocarbon groups on the siloxane drive petroleum sources. The term includes, for example, a petrolatum, a microcrystalline wax, a thickened and gelled mineral oil or mixtures thereof. These materials are all commercially available.

Petrolatum is a soft, unctious, semi-solid material containing relatively high amounts of oil. As a gel or jelly, it is a colloidal system of nonstraight-chain solid hydrocarbons and high-boiling liquid hydrocarbons, in which most of the liquid hydrocarbons are held inside the micelles. As a liquid, it comprises a mixture of liquid hydrocarbons from petroleum and is known as mineral oil or white mineral oil.

A microcrystalline wax is higher melting material refined from "petrolatum" by reducing the oil content through solvent separation steps "deoiling" to very low levels traditionally in the 1 to 5% range. The refined waxes are then decolorized to produce white or very light colored materials called microcrystalline waxes. Microcrystalline waxes contain hydrocarbon chains having a molecular weight range of about 500 to 800 and contain n-alkane, isoalkane, waxes contain hydrocarbon chains having a molecular weight range of about 500 to 800 and contain n-alkane, isoalkane, and cycloalkane factors. Melting point of the waxes may vary from about 140° F. to over 210° F.

As representative and preferred petrolatums of the present invention are, for example, those available from Penreco, Kairns City, Pa., called White Petrolatum USP which comprises any of six products in the series. The most preferred is Penreco Ultima White which has a melting point of 130/140° F., viscosity SUS at 210° F. of 60/70°.

As a representative and preferred embodiment of a microcrystalline wax of the present invention is Ultraflex® Amber Wax available from Bareco Products, Rock Hill, S.C. The material has a specific gravity at 16° C. of 0.93 a melting point of 69° C., and a viscosity at 99° C. of 13 cP.

As representative and preferred embodiments of thickened and gelled white mineral oils are those available from Penreco, Kairns City, Pa., called Geahlene®. The products are a group of hydrocarbon based materials of the liquid petrolatum type used in the pharmaceutical and cosmetic industry. The CTFA name for the products is "Mineral Oil (and) Hydrogenated Butylene/Ethylene/Styrene Copolymer (and) Hydrogeneated Ethylene/Propylene/Styrene Copolymer." These materials may vary in viscosity from 20,000 to 160,000 cPs at 25° C. and have a specific gravity of 0.82 at 25° C. The most preferred of this series in Geahlene® 1600 which has the high viscosity range.

The term "fat like petroleum based carrier" used throughout the specification and in the claims refers to the composition of the present invention without the active ingredient, the insecticide. The carrier is the diluent, excipient or matrix which contains, protects, supports or envelopes the insecticide. The "fat like petroleum based carrier" thus includes as the essential component the petroleum based carriers defined above but may also contain, if desired, preservatives, flowing agents, and the like. The "carrier" may also preferably contain attractants and feeding stimulants depending on the targeted pest. Feeding stimulants are, for example, carbohydrates, carbohydrate complexes. Examples of carbohydrates are maltodextrins and the like; carbohydrate complexes, corn syrup solids, protein such as yeast extracts, milk solids, sugars such as sucrose, glucose, fructose, starches such as corn, potato and the like. Examples of attractants are odorants and flavorants such as, for example, cyclotenes and the like, plant extracts such as fenugreek and the like, alcohols such as ethanol, or a volatile ester in combination with ethanol. Said volatile ester is made from a combination of a $C_1$–$C_6$ branched or unbranched alcohol with a $C_1$–$C_3$ carboxylic acid. Lower alcohols useful in the manufacture of the volatile ester co-attractants of the invention include methyl alcohol, ethyl alcohol, n-propyl alcohol, isopropyl alcohol, n-butyl alcohol, isobutyl alcohol, tertiary butyl alcohol, n-amyl alcohol, isoamyl alcohol, tertiary amyl alcohol, n-hexyl alcohol, and mixtures thereof, etc. Carboxylic acids useful in manufacturing the ester attractant of the invention include acetic acid, propionic acid, butyric acid, mixtures thereof, and others. The associated reactive analogs of the respective carboxylic acids can be used, for example, the acid chloride or acid anhydride. The preferred volatile ester for use is a lower alcohol acetate ester such as n-amyl acetate, isoamyl acetate, isobutyl acetate, n-propyl acetate, ethyl acetate or mixtures thereof. Some of the ingredients may overlap in category as they can be both attractants and feed stimulants, for example proteins mentioned above, odorants and flavorants.

While any insecticide can be used in the present invention including the classes of insecticides defined above, those particularly named among the classes constitute preferred embodiments. An effective amount of insecticide may vary depending on the choice of insecticide and the targeted pest. For example, for the classes of insecticides defined above, with the exception of boric acid, an effective amount of insecticide may be as low as about 0.001 wt % of the composition. Thus, a range of such insecticide to provide an effective amount may be from about 0.001 wt % to about 5.0 wt %. Acephate, chlorpyrifos, cyfluthrin, deltamethrin, and propoxur are preferred, chlorpyrifos being the most preferred. Acephate is a fine crystalline powder that is water soluble and can be incorporated easily into a fat like petroleum based forming a suspension or paste. Acephate is also desirable as an active ingredient since there is no known insecticide resistance and it has very low repellency and mammalian toxicity. The other preferred active ingredients can also be incorporated easily into a fat like petroleum based forming a suspension or paste. Such formulations are very stable and have enhanced palatability and efficacy.

A preferred embodiment of the present invention includes a water-free insecticidal composition including about 0.001–5.0 wt % of an insecticide selected from the group consisting of an organophosphate, a carbamate, a pyrethroid, an amidinohydrazone, an avermectin, and a chlorinated hydrocarbon, and about 20–60 wt-% of a fat like petroleum based carrier.

A more preferred composition comprises about 0.001–5.0 wt % of an insecticide selected from the group consisting of acephate, chlorpyrifos, propoxur, cyfluthrin, deltamethrin, hydramethylnon, abamectin, and lindane and about 20–60 wt-% of a fat like petroleum based carrier.

Another preferred embodiment is a water-free insecticidal composition comprising about 5–60 wt % boric acid, and about 20–60 wt % of a fat like petroleum based carrier.

As an example of a preferred insecticide fat-like petroleum based bait formulation, other than boric acid, the following composition is representative:

(i) about 0.001–5 wt-% of insecticide;

As representative of the present invention, a list of preferred fat like petroleum based carriers including feeding stimulants and attractants with preferred ranges in weight percentages is provided in Table I. The last entry is not a preferred carrier of the present invention but a water-based carrier (Xanthan Gum) used in the examples for comparison purposes.

TABLE I

| INGREDIENT | FUNCTION | SUPPLIER/ CONTACT | % RANGE IN BAIT |
|---|---|---|---|
| TASTONE 154 Primary Yeast Extract Powder | Feeding Stimulant (Protein) | Red Star Bio Prdcts. Juneau, Wisconsin | 5.0–20.0 |
| TASTONE 310 Primary Yeast Extract Powder | Feeding Stimulant (Yeast Protein) | Red Star BioPrdcts. Juneau, Wisconsin | 5.0–20.0 |
| TASTONE 900 Primary Yeast Extract | Feeding Stimulant (Yeast Protein) | Red Star BioPrdcts. Juneau, Wisconsin | 5.0–20.0 |
| STD.DARK POWDER Autolized Yeast Extract #8001 | Feeding Stimulant (Yeast Protein) | FIDCO Solon, OH | 5.0–20.0 |
| LIGHT MALT EXTRACT Code 87 Powder | Feeding Stimulant (Malt Proteins % Carbohydrate | Malt Products Corp. Saddle Brook, NJ | 15.0–30.0 |
| WHEY PROTEIN CONC. 50.0% Protein Powder 050 #5623 | Feeding Stimulant (Milk Protein) | Century Foods Sparta, WI | 20.0–40.0 |
| WHEY PROTEIN CONC. 34.0% Protein Powder 034 #5623 | Feeding Stimulant (Milk Protein & Carbohydrate) | Century Foods Sparta, WI | 20.0–40.0 |
| PROMINE DS Soy Protein Conc. Powder Code 3210 | Feeding Stimulant Filler (Soy Protein) | Central Soya Ft. Wayne, IN | 5.0–30.0 |
| FRODEX 42 Corn Syrup Solids Granular Fine Powder | Feeding Stimulant (Carbohydrate) | AMAIZO American Maine Products | 10.0–30.0 |
| NAT. YEAST FLAVOR #340797 Liquid | Atractant and Feeding Stimulant | Tastemaker Cincinnati, OH | 0.25–1.0 |
| N&A TOASTED CEREAL FLAVOR PK-2012 Liquid | Attractant and Feeding Stimulant | Flavor Materials Intnl. Avenel, New Jersey | 0.1–0.5 |
| NAT. BUTTER FLAVOR PK-233 Liquid | Attractant and Feeding Stimulant | Flavor Materials Intnl. Avenel, New Jersey | 0.05–0.2 |
| NAT. SWEET CREAM PK-225 Liquid | Attractant and Feeding Stimulant | Flavor Materials Intnl. Avenel, New Jersey | 0.1–0.5 |
| ULTIMA WHITE Petrolatum | Bait Base (Pet Oil) | Penreco Karns City, PA | 20.0–60.0 |
| GEAHLENE Gelled Mineral Oil | Bait Base (Pet. Oil) | Penreco Karns City, PA | 20.0–60.0 |
| ULTRAFLEX AMBER Mitracrystalline Wax | Bait Base (Pet. Oil) | Bareco Products Rock Hill, SC | 20.0–60.0 |
| RHODOPOL 23 Xanthan Gum | Base Base (Water) | R. T. Vanderbilt Co., Inc. Norwalk, CT | 20.0–60.0 of 15.0% solution |

(ii) about 20–60 wt-% of a fat like petroleum based carrier;

(iii) about 5–40 wt-% of a feed stimulant, and (iv) about 0.05–1 wt-% of an insect attractant.

As an example of a preferred boric acid fat-like petroleum based bait formulation, the following composition is representative:

(i) about 5–60 wt-% boric acid;

(ii) about 20–60 wt-% of a fat like petroleum based carrier;

(iii) about 5–40 wt-% of a feed stimulant, and (iv) about 0.05–1 wt-% of an insect attractant.

As a paste, the above described compositions can be used as containerized or non-containerized baits, the application depending on the targeted pest. As an example, paste formulations may be applied in cracks and crevices of apartments, homes or industrial settings where pests, especially cockroaches and ants are likely to reside. Pastes are applied into cracks and crevices, for example, in the kitchens and bathrooms of the above structures for effective control and killing of these pests. The pastes can be manufactured by well-known methods which essentially comprise blending the active insecticide into the fat like petroleum based carrier as described above. Additional ingredients, if desired, are also added during the blending operation.

The following examples are used to illustrate the present invention but are not limiting thereon.

EXAMPLES

The following fat like petroleum based bait formulations were prepared as described in detail in Table II along with a water-based bait formulation. The petroleum based formulations were tested for stability (browning) and palatability and compared with water-based baits. The results are shown in FIGS. 1, 2, 7, 8, 12, 13, 17, 18, 22, 23, 27 and 28. All petroleum based baits were more stable and had enhanced palatability after eight days at 122° F. than a water-based bait.

Figure 3:
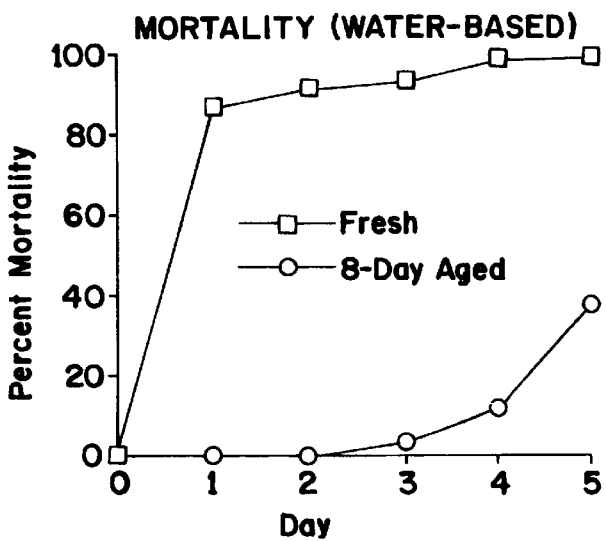
Figure 4:
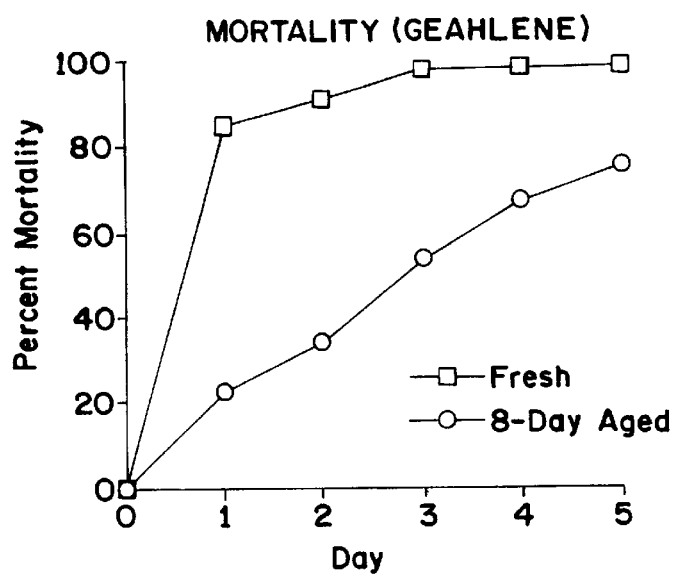
Figure 5:
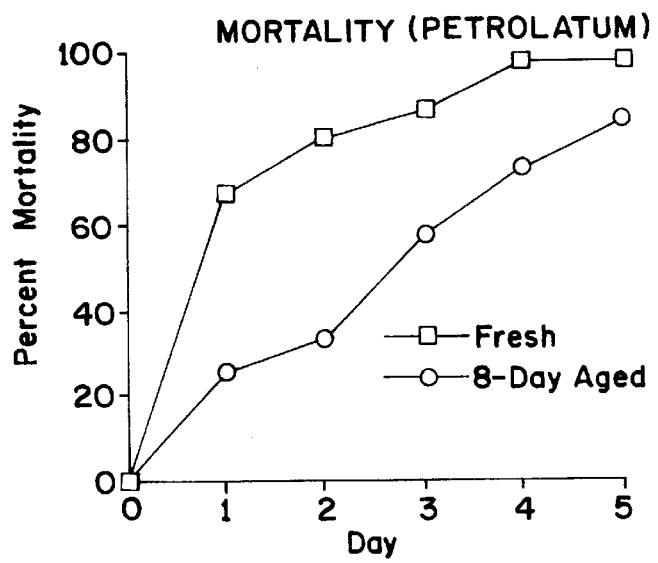
Figure 6:
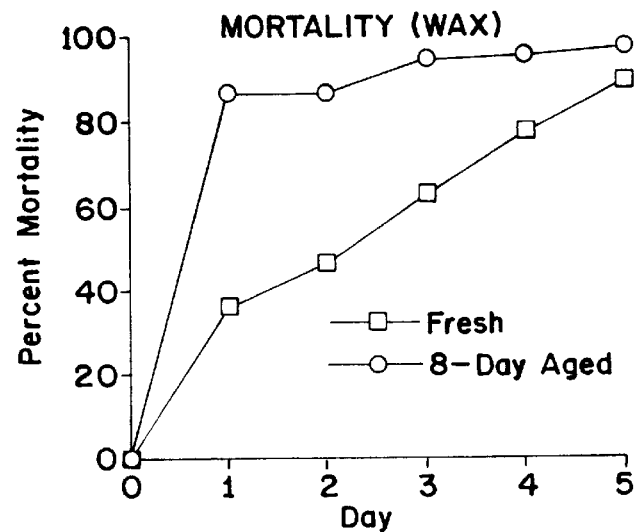
Figure 7:
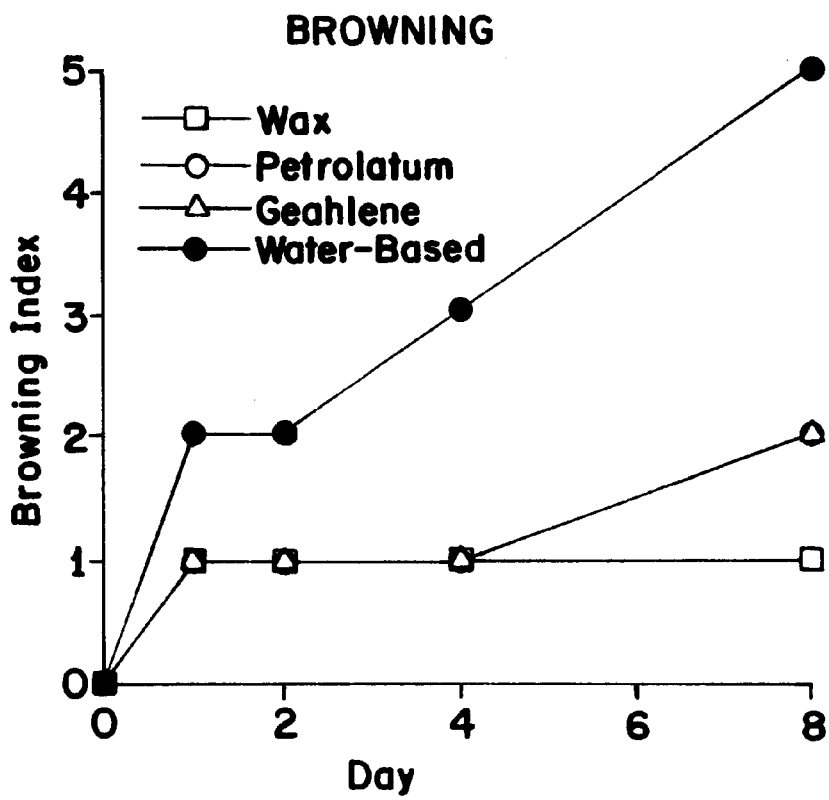
FIGS. 7 through 11 show graphic results of studies using boric acid as the insecticide.
Figure 8:
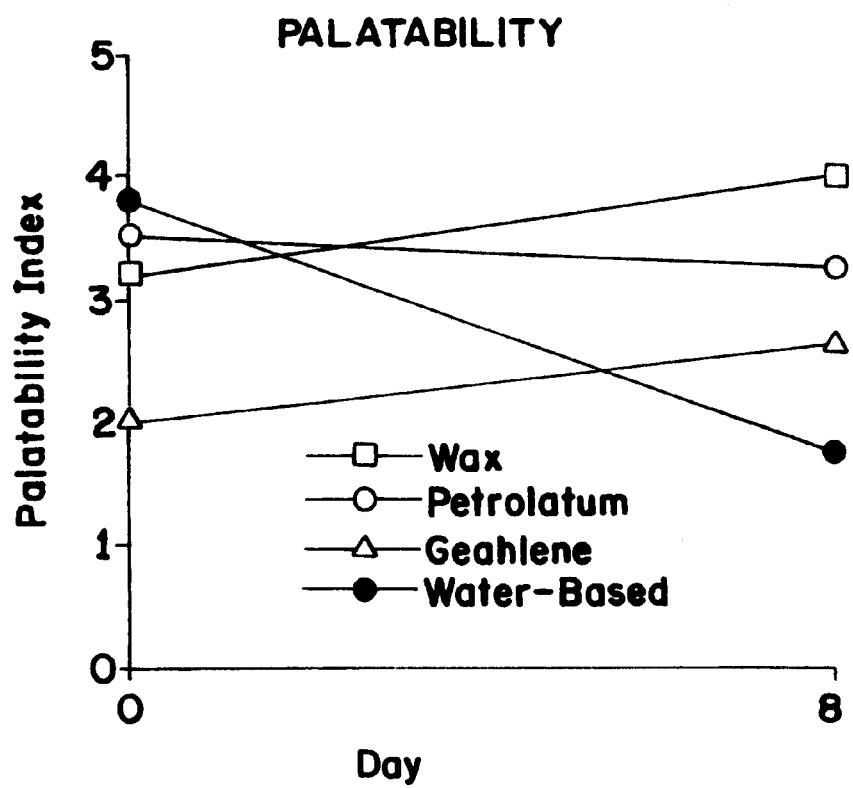
Figure 9:
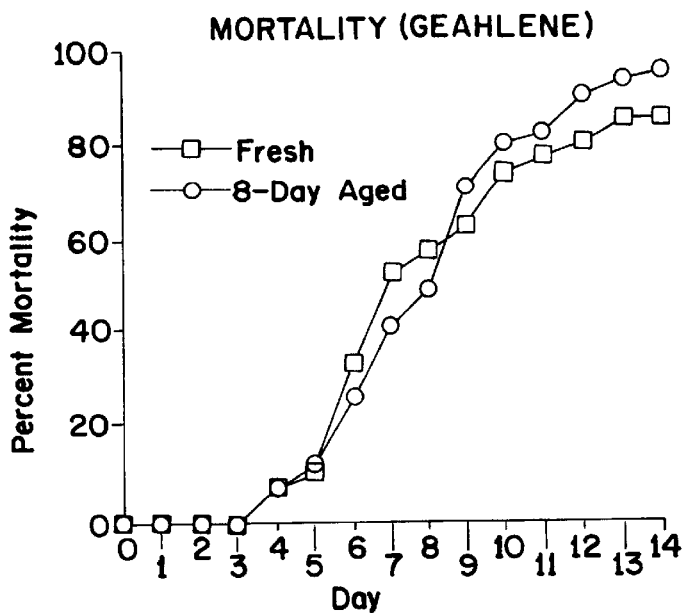
Figure 10:
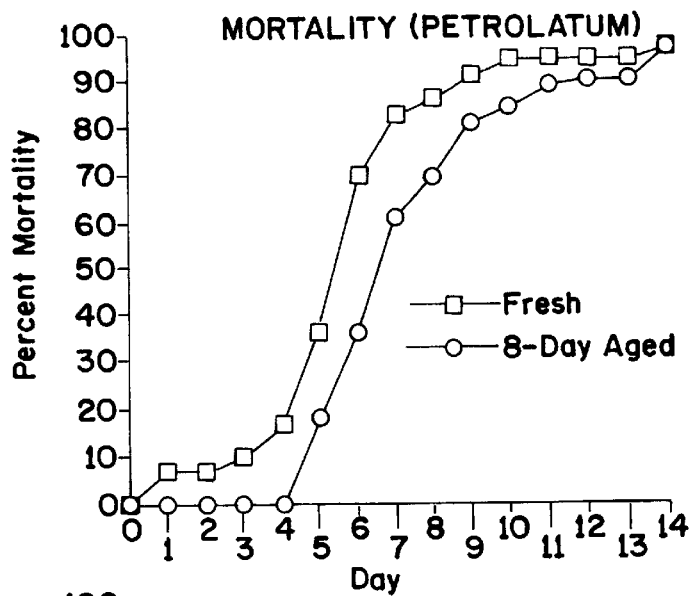
Figure 11:
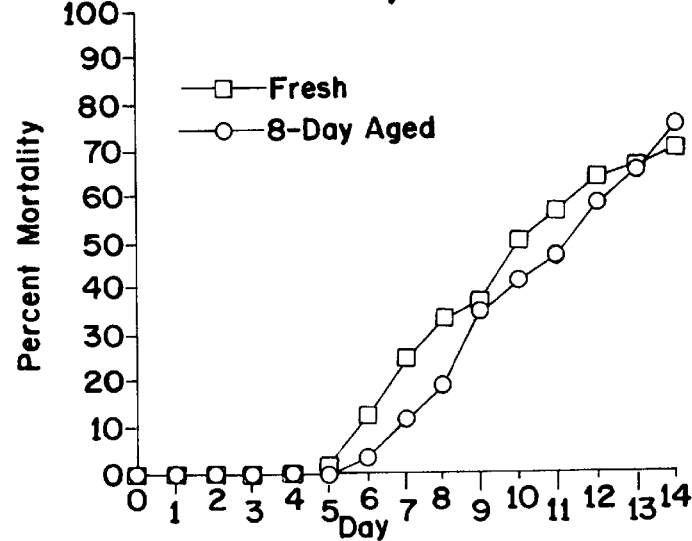
Figure 13:
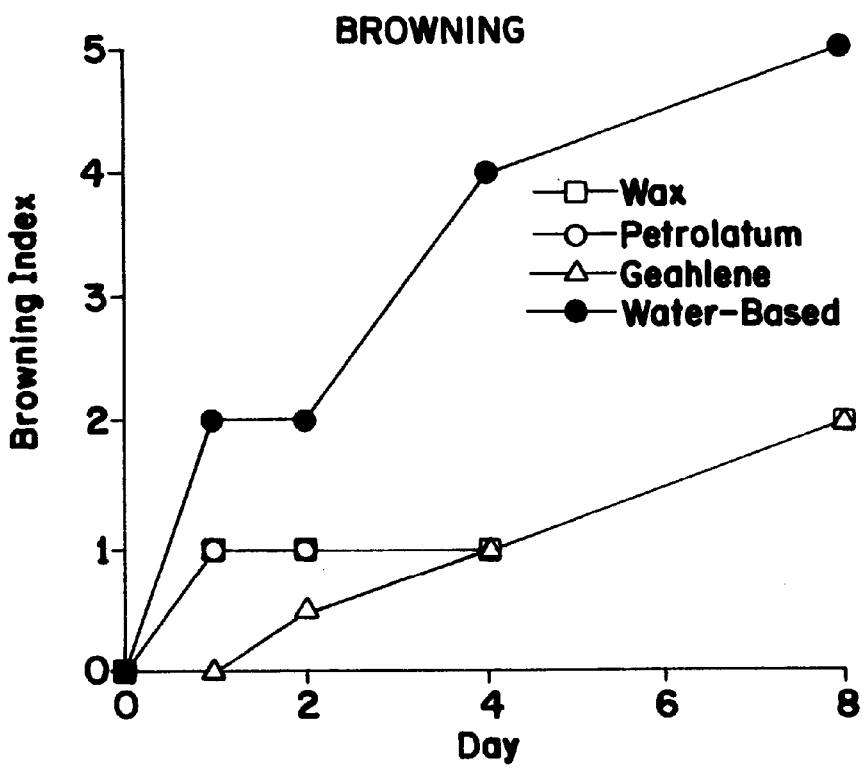
Figure 14:
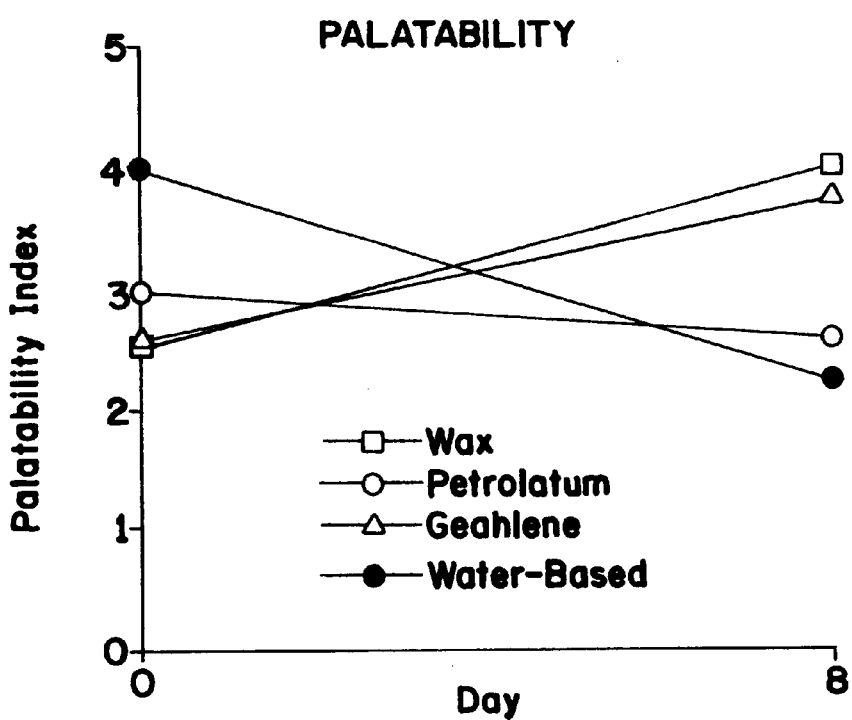
Figure 15:
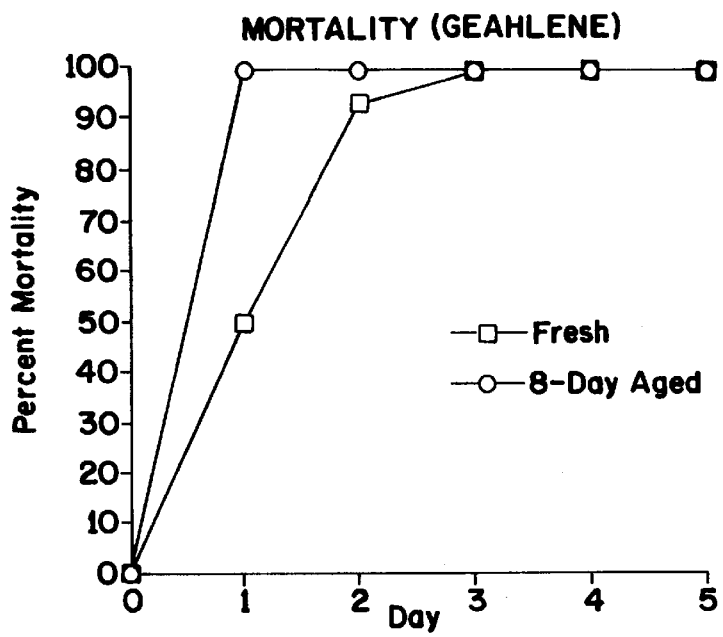
Figure 16:
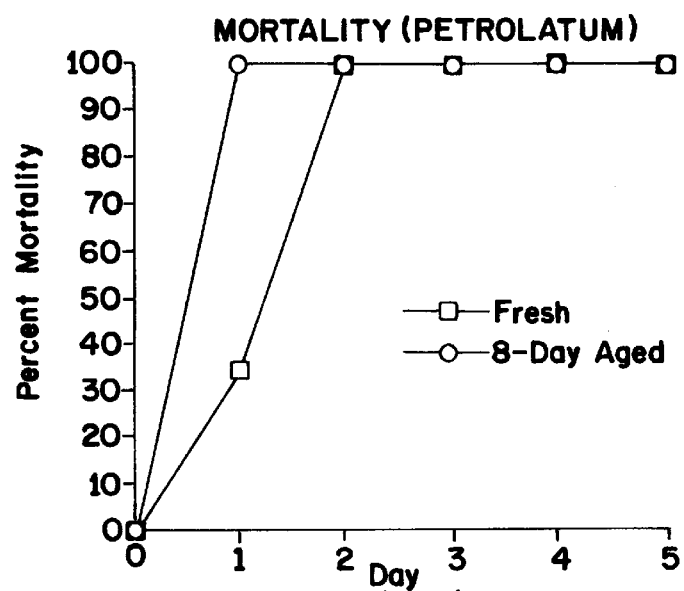
Figure 17:
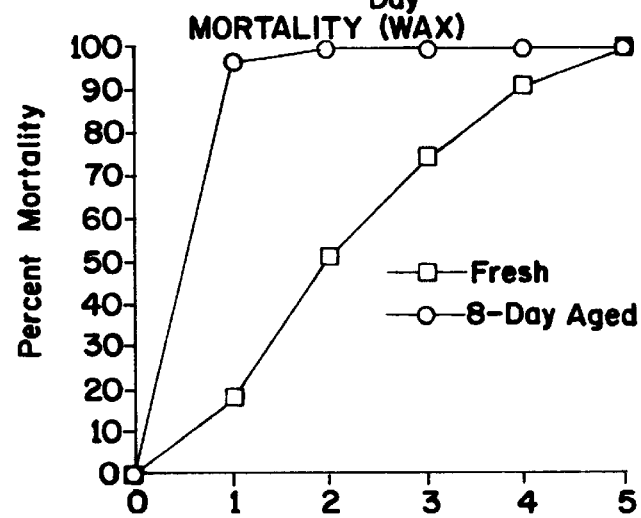
FIGS. 17 through 21 show graphic results of studies similar to those shown in FIGS. 7 through 16 where cyfluthrin is the insecticide.
Figure 18:
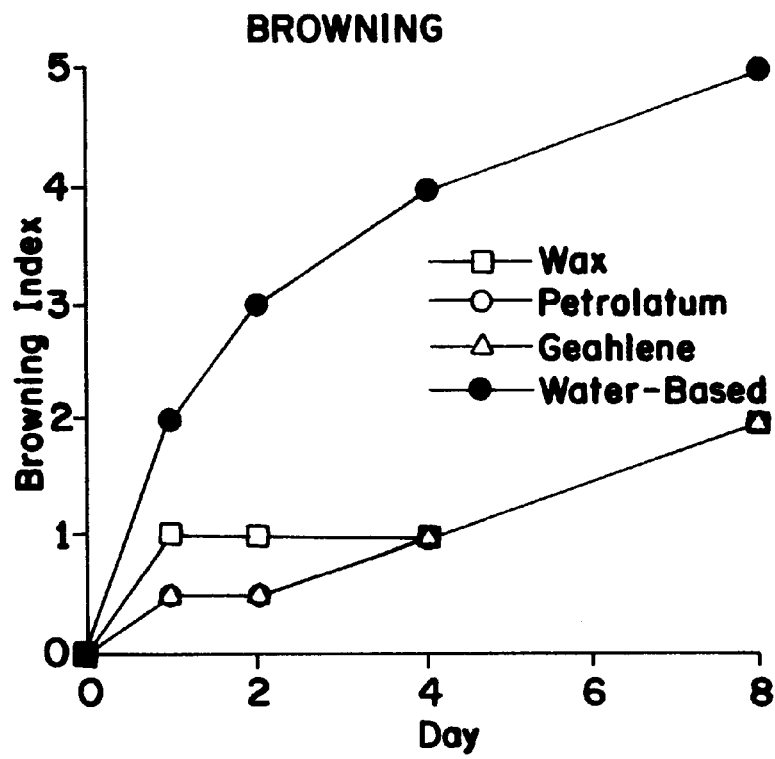
Figure 19:
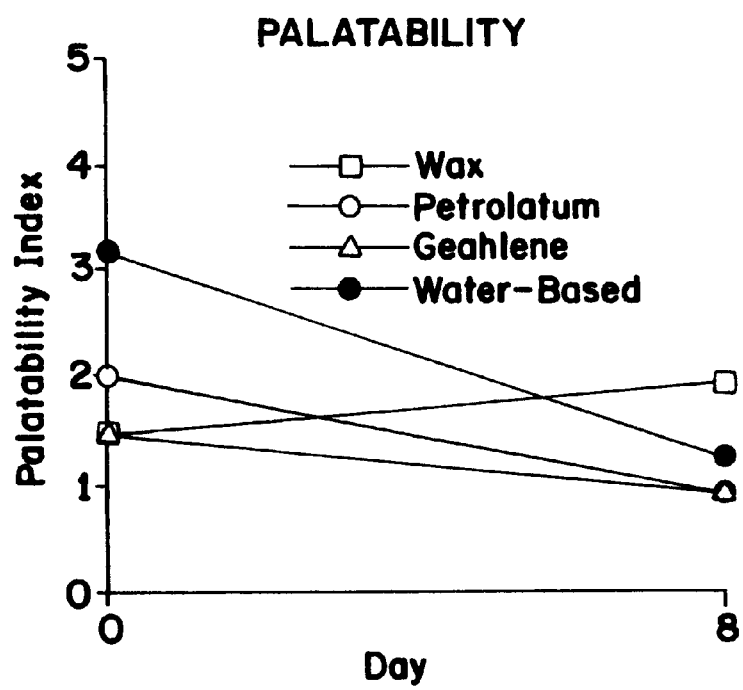
Figure 20:
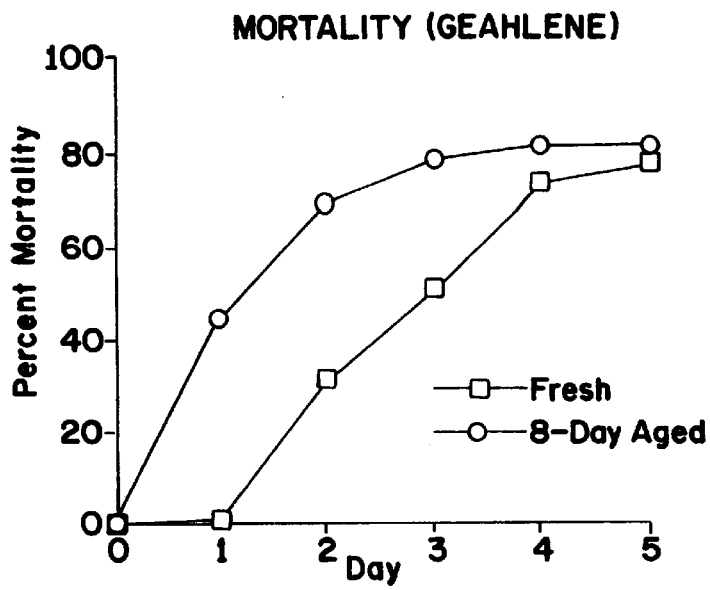
Figure 21:
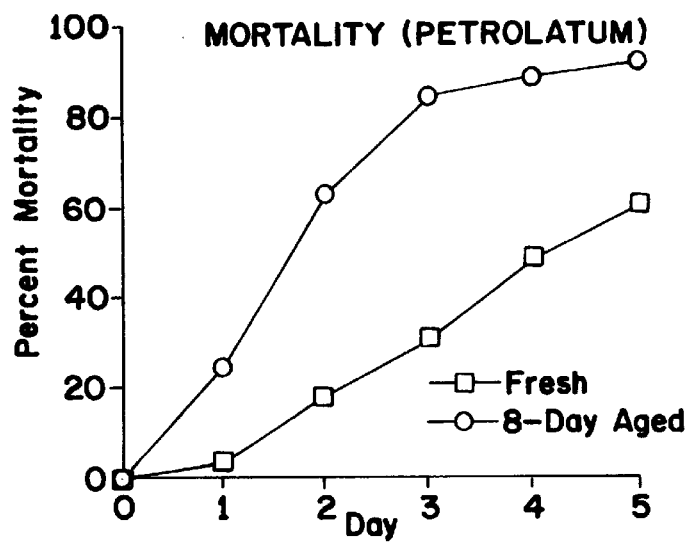
Figure 22:
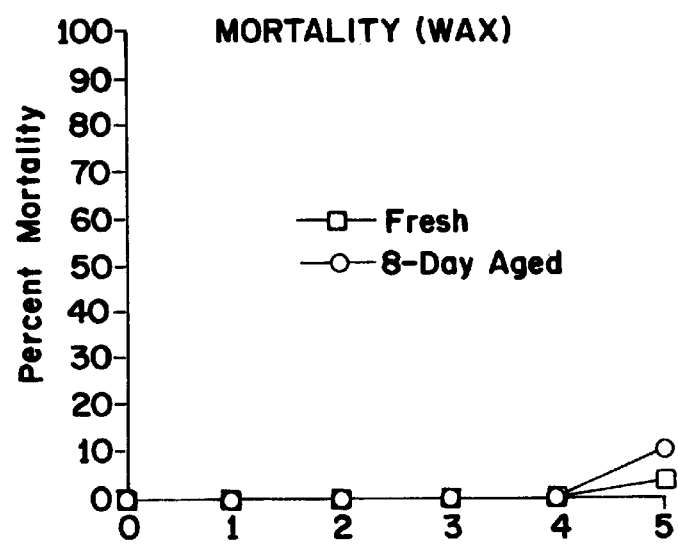
FIGS. 22 through 26 show graphic results of studies similar to those shown in FIGS. 7 through 21 where deltamethrin is the insecticide.
Figure 23:
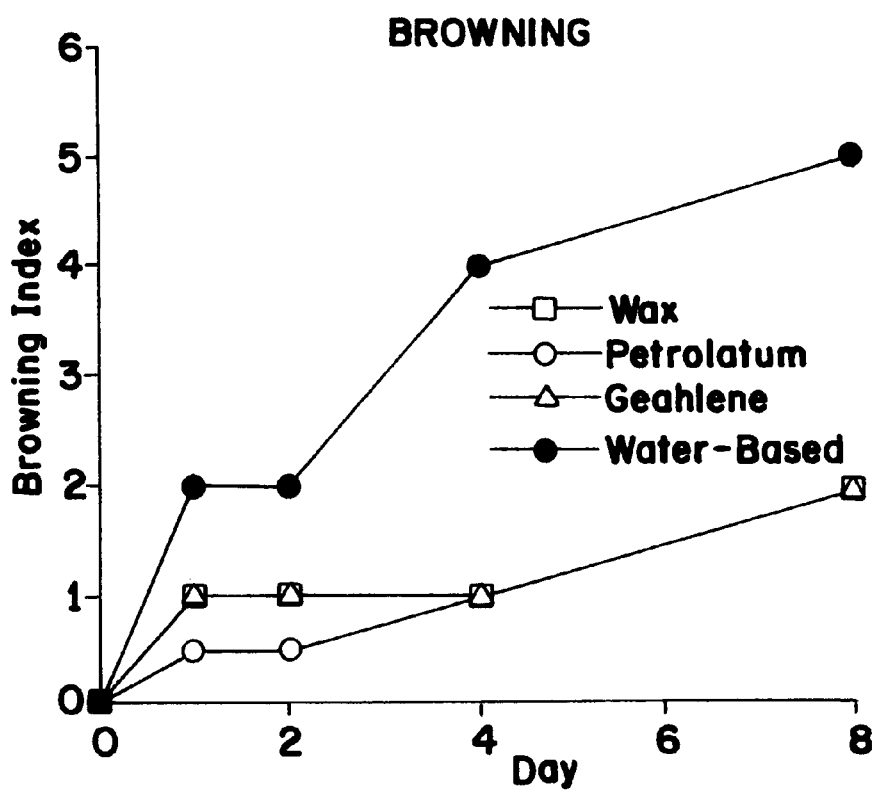
Figure 24:
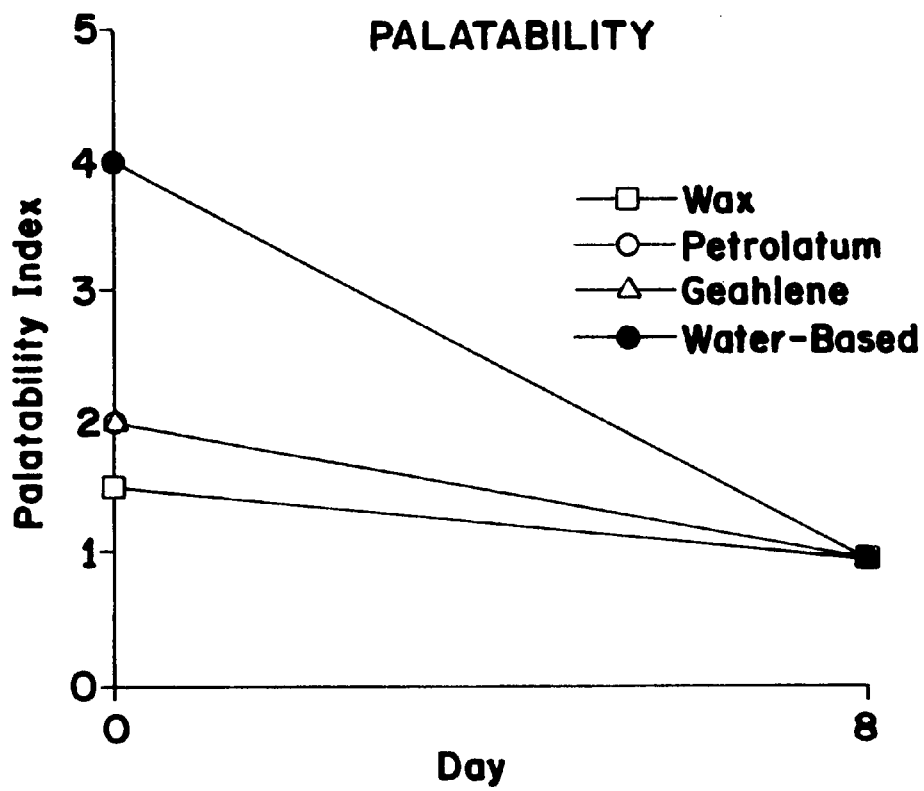
Figure 25:
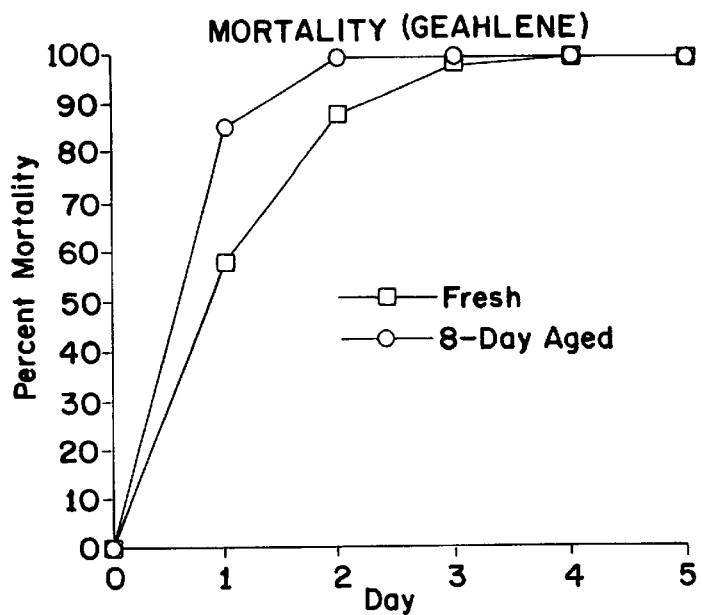
Figure 26:
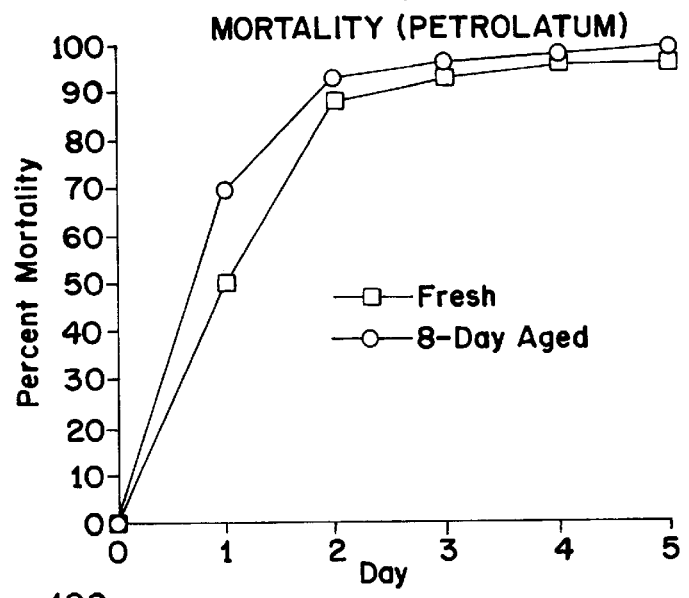
Figure 27:
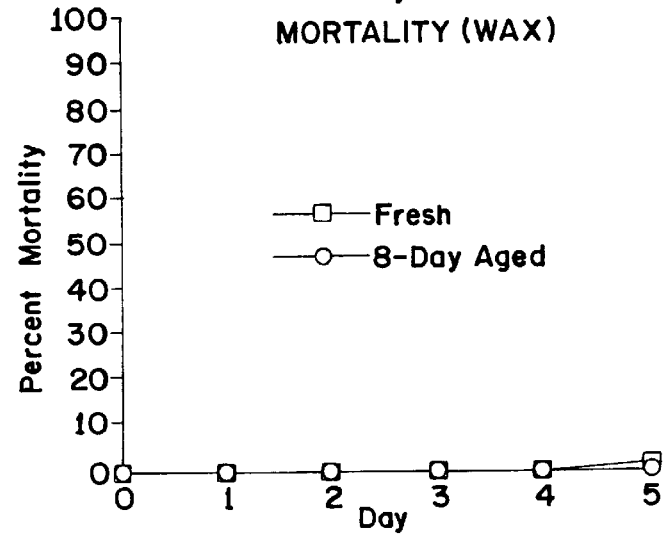
FIGS. 27 through 31 show graphic results of studies similar to those shown in FIGS. 7 through 26 where propoxur is the insecticide.
Figure 28:
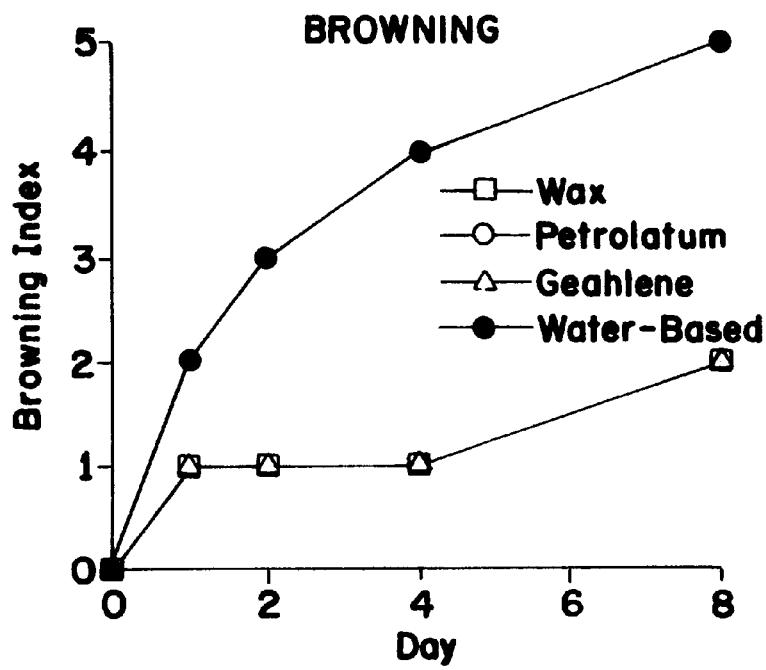
Figure 29:
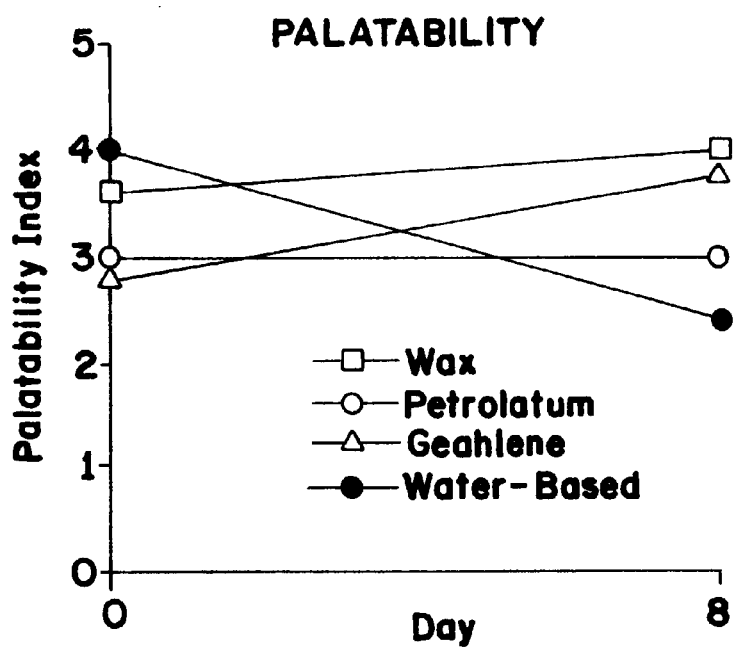
Figure 30:
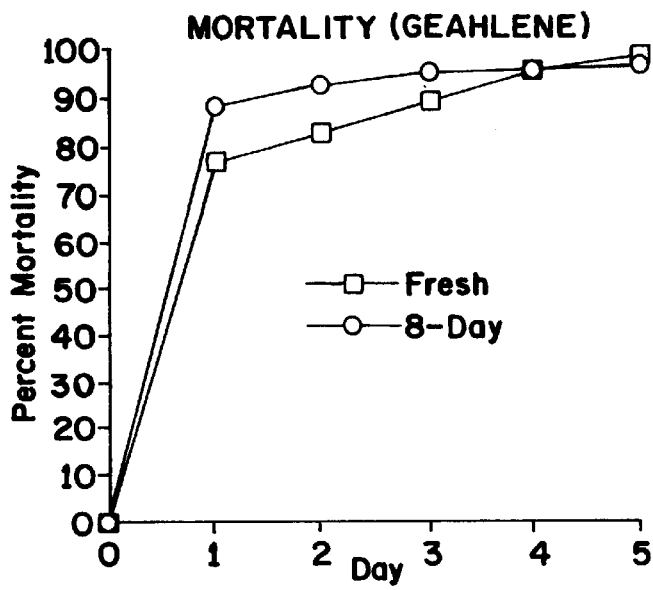
Figure 31:
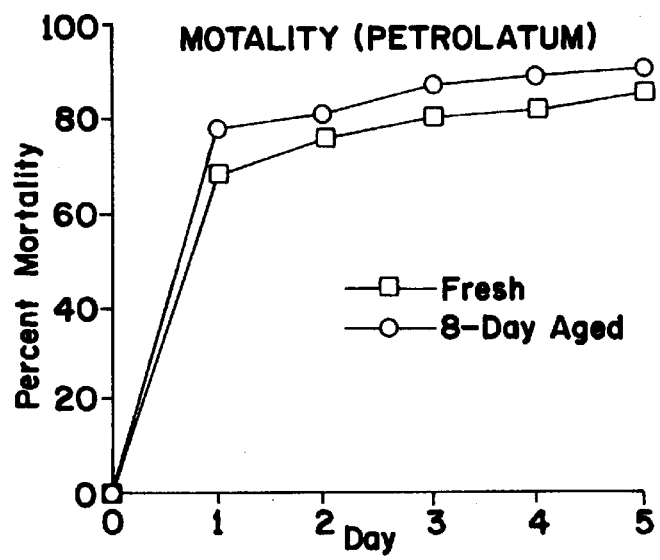
Figure 32:
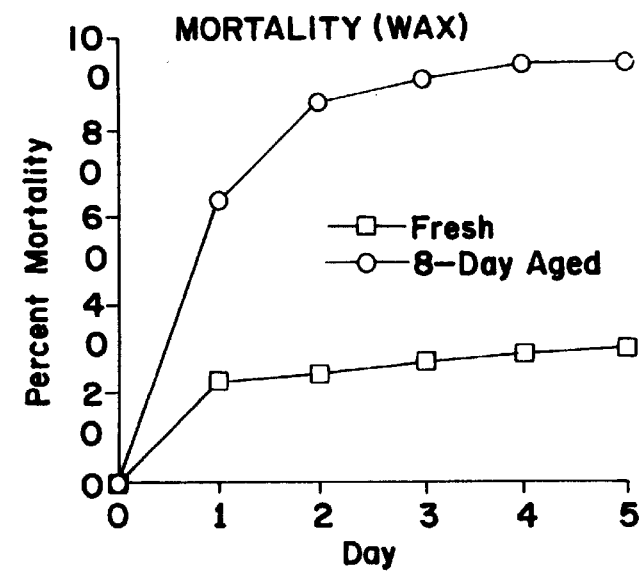

Efficacy studies were carried out starting each test with fresh bait preparations and 8-day aged preparations for each fat like petroleum based composition of Table II and reported as percent mortality vs. days observed. The same test was also carried out with an acephate water-based formulation (Table II). The results are shown in FIG. 3, (acephate, water-based), FIGS. 4–6 (acephate), 9–11 (boric acid), 14–16 (chlorpyrifos), 19–21 (cyfluthrin), 24–26 (deltamethrin), and 29–31 (propoxur). The efficacy of fresh samples of petroleum based and water based acephate formulations were about the same whereas the 8-day aged sample of petroleum based acephate provided a greater kill than the corresponding water-based acephate bait.

METHODS FOR BAIT EVALUATIONS

Test for Heat Stability (Browning)

Purpose

To determine relative color and/or viscosity changes of bait formulations from accelerated aging treatments.

Materials

1. Bait formulas from Table II for screening.
2. 50.0 ml translucent glass vials or similar containers for bait storage.
3. Mettle spatula for mixing and placing bait into vials.
4. Balance for measuring bait and touch-testing bait viscosity/texture.
5. Blue M or similar oven for aging vials of bait @ 122° F. continuously.

Methods

1. Using the spatula, 5.0 g of bait was smeared onto the top section of a vial, such that the bait adhered firmly to the wall of the vial. Prepared 2 vials per bait formula and labelled with formula no. and the date of time zero.
2. Placed one vial in the oven and aged for appropriate time period at 122° F. Kept the other vial at room temperature and used for comparing color and viscosity changes with the aged vial.
3. Removed the aged vials from the oven at day 1, 2, 4 and 8 and made visual observations of discoloration (usually browning) and viscosity changes (usually decreased

TABLE II

| Active Ingredient | *Microcrystalline Wax (Ultraflex Amber) | Petrolatum (Ultima White) | Gelfed Mineral Oil (Geahlene) | **Water-Based (Xanthan Gum) |
|---|---|---|---|---|
| Boric Acid 30.0% | 30.0% Wax<br>30.0% Boric Acid<br>20.0% Frodex42<br>20.0% Primary Yeast | 30.0% Ultima White<br>30.0% Boric Acid<br>20.0% Frodex42<br>20.0% Primary Yeast | 30.0% Geahlene<br>30.0% Boric Acid<br>20.0% Frodex42<br>20.0% Primary Yeast | 30.0% Xanthan/Water<br>30.0% Boric Acid<br>20.0% Frodex42<br>20.0% Primary Yeast |
| Deltamethrin 0.05% | 40.0% Wax<br>19.0% Promine DS<br>20.0% Primary Yeast<br>1.0% Suspend = 0.05% | 40.0% Ultima White<br>19.0% Promine DS<br>20.0% Primary Yeast<br>1.0% Suspend = 0.05% | 35.0% Geahlene<br>24.0% Promine DS<br>20.0% Primary Yeast<br>1.0% Suspend = 0.05% | 40.0% Xanthan/Water<br>19.0% Promine DS<br>20.0% Primary Yeast<br>1.0% Suspend = 0.05% |
| Propoxur 1.0% | 40.0% Wax<br>19.0% Promine<br>20.0% Frodex 42<br>20.0% Primary Yeast<br>1.0% Propoxur | 40.0% Ultima White<br>19.0% Promine<br>20.0% Frodex 42<br>20.0% Primary Yeast<br>1.0% Propoxur | 35.0% Geahlene<br>24.0% Promine<br>20.0% Frodex 42<br>20.0% Primary Yeast<br>1.0% Propoxur | 40.0% Xanthan/Water<br>19.0% Promine<br>20.0% Frodex 42<br>20.0% Primary Yeast<br>1.0% Propoxur |
| Chlorpyrifos 0.5% | 40.0% Wax<br>19.5% Promine<br>20.0% Frodex 42<br>20.0% Primary Yeast<br>0.5% chlorpyrifos | 40.0% Ultima White<br>19.5% Promine<br>20.0% Frodex 42<br>20.0% Primary Yeast<br>0.5% chlorpyrifos | 35.0% Geahlene<br>24.5% Promine<br>20.0% Frodex 42<br>20.0% Primary Yeast<br>0.5% chlorpyrifos | 40.0% Xanthan/Water<br>19.5% Promine<br>20.0% Frodex 42<br>20.0% Primary Yeast<br>0.5% chlorpyrifos |
| Cyfluthrin 0.05% | 40.0% Wax<br>19.75% Promine<br>20.0% Frodex 42<br>20.0% Primary Yeast<br>0.25% Tempo 20WP = 0.05% active | 40.0% Ultima White<br>19.75% Promine<br>20.0% Frodex 42<br>20.0% Primary Yeast<br>0.25% Tempo 20WP = 0.05% active | 35.0% Geahlene<br>24.75% Promine<br>20.0% Frodex 42<br>20.0% Primary Yeast<br>0.25% Tempo 20WP = 0.05% active | 40.0% Xanthan/Water<br>19.75% Promine<br>20.0% Frodex 42<br>20.0% Primary Yeast<br>0.25% Tempo 20WP = 0.05% active |
| Acephate 1.0% | 40.0% Wax<br>18.96% Promine DS<br>20.0% Frodex 42<br>20.0% Primary Yeast<br>1.04% Orthene PCO II = 1.0% active | 40.0% Ultima White<br>18.96% Promine DS<br>20.0% Frodex 42<br>20.0% Primary Yeast<br>1.04% Orthene PCO II = 1.0% active | 35.0% Geahlene<br>23.9% Promine DS<br>20.0% Frodex 42<br>20.0% Primary Yeast<br>1.04% Orthene PCO II = 1.0% active | 40.0% Xanthan/Water<br>18.96% Promine DS<br>20.0% Frodex 42<br>20.0% Primary Yeast<br>1.04% Orthene PCO II = 1.0% active |

*Microcrystalline wax must be heated to 160° F. before adding preblends as discussed below. Mix until bait hardens slightly.
**Prepare 15.0% Xanthan/85% water base by slowly adding xanthan gum to water until gelled (mix 20 min at ambient temp.) This "water-based" medium has a viscosity similar to the petrolatum (Ultima White).
1. Boric Acid Baits: Preblend all powders and add to base. Add boric acid last and mix thoroughly until homogeneous.
2. Deltamethrin Baits: Preblend all powders, add to base and mix until homogeneous. Add Suspend (deltamethrin concentrate) last.
3. Propoxur Baits: Grind technical propoxur to a fine powder and add to preblend. Add preblend to base and mix thoroughly.
4. Chlorpyrifos: Preblend powders and add to base. Melt chlorpyrifos (110° F.), add last and mix thoroughly.
5. Cyfluthrin: Add Tempo 20WP cyfluthrin concentrate to preblend and add to base. Mix thoroughly.
6. Acephate: Grind Orthene PCO II acephate concentrate to a powder and add to preblend. Add preblend to base and mix thoroughly.

viscosity=melt or softening, sometimes increased viscosity=hardening), using the room temperature vial for comparison.

4. Rated observations of browning. For browning, rate from 0.0 to 5.0 represents "no change" to "significant browning" for the bait respectively.

Test for Screening Palatability and Efficacy (Mortality) of Cockroach Baits

Purpose

To determine relative palatability and effectiveness of bait formulations to German cockroach, *Blattella germanica* (L.).

Materials

1. Bait formulas for screening. (Formulations from Table II).
2. Mason jars coated on the upper lip with petrolatum to prevent escape.
3. Mettle spatula for mixing and applying bait.
4. Balance for measuring bait.
5. German cockroaches; 10 per jar.
6. Stop watch.
7. Test formulas (fresh or aged for eight days at 122° F.).

Methods

1. Allowed 4 hours for German cockroaches to acclimate with food and water in the jars. Allowed alternative food and water to be present during testing period.
2. Applied 0.3 g of bait to one lip of an inverted plastic weigh boat (simulated crack & crevice treatment).
3. Following acclimation, ca, 4 hours, placed the baited (and inverted) weigh boat flatly into the jar. Repeated for all cockroach jars in sequence.
4. For each jar containing a baited weigh boat, ranked visual observations of attractiveness and palatability from 1.0–5.0 (1.0=least attractive or palatable; 5.0=most attractive or palatable). Allowed for 2.0 min of observation time and six replications of each treatment combination (six weigh boats in six separate jars for each life stage).
5. Measured the number of moribund cockroaches each day post exposure and recorded percent mortality over time.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A water-free insecticidal composition for use against insect pests consisting essentially of:
   about 0.001–5.0 wt-% of acephate;
   about 20–60 wt-% of a petroleum based carrier selected from the group consisting of a gelled mineral oil, a microcrystalline wax, a petroleum and mixtures thereof;
   about 5–40 wt-% of a feeding stimulant; and
   about 0.005–1 wt-% of an insect attractant.

2. An insecticidal bait composition for use against insect pests with improved stability and palatability consisting essentially of:
   (a) about 20–60 wt-% of a petroleum based carrier selected from the group consisting of a gelled mineral oil, a microcrystalline wax, a petrolatum and mixtures thereof; and
   (b) about 0.001–5.0 wt-% of acephate,
wherein the composition is substantially free of water and is in the form of a paste.

* * * * *

UNITED STATES PATENT AND TRADEMARK OFFICE
CERTIFICATE OF CORRECTION

PATENT NO. : 5,914,105

DATED        : JUNE 22, 1999

INVENTOR(S) : BARCAY ET AL.

It is certified that error appears in the above-identified patent and that said Letters Patent is hereby corrected as shown below:

Col. 5, Table I, column "INGREDIENT", third line from bottom of table: "Mitracrystalline" should read —Microcrystalline—

Col. 5, Table I, column "SUPPLIER/CONTACT", line 21 of table: "Maine" should read —Maize—

Col. 7, Table II: column heading "Gelfed" should read —Gelled—

Col. 10, line 21, claim 1: "0.005" should read —0.05—

Signed and Sealed this

Twelfth Day of December, 2000

*Attest:*

Q. TODD DICKINSON

*Attesting Officer*        *Director of Patents and Trademarks*